(12) United States Patent
Pathi et al.

(10) Patent No.: US 8,269,003 B2
(45) Date of Patent: Sep. 18, 2012

(54) STABLE CRYSTAL FORM OF IMATINIB MESYLATE AND PROCESS FOR THE PREPARATION THEREOF

(75) Inventors: Srinivas Laxminarayan Pathi, Bangalore (IN); Revikumar Puppala, Bangalore (IN); Rajendra Narayanrao Kankan, Mumbai (IN); Dharmaraj Ramachandra Rao, Mumbai (IN)

(73) Assignee: CIPLA Limited, Mumbai (IN)

( * ) Notice: Subject to any disclaimer, the term of this patent is extended or adjusted under 35 U.S.C. 154(b) by 937 days.

(21) Appl. No.: 11/574,642

(22) PCT Filed: Sep. 2, 2005

(86) PCT No.: PCT/GB2005/003392
§ 371 (c)(1),
(2), (4) Date: May 23, 2007

(87) PCT Pub. No.: WO2006/024863
PCT Pub. Date: Mar. 9, 2006

(65) Prior Publication Data
US 2007/0265288 A1    Nov. 15, 2007

(30) Foreign Application Priority Data
Sep. 2, 2004    (IN) .............................. 951/MUM/2004

(51) Int. Cl.
*C07D 411/00*    (2006.01)
(52) U.S. Cl. ...................... 544/333; 544/360; 546/268.1
(58) Field of Classification Search .................. 544/333, 544/360; 546/268.1
See application file for complete search history.

(56) References Cited

U.S. PATENT DOCUMENTS
5,521,184 A    5/1996 Zimmermann

FOREIGN PATENT DOCUMENTS
| | | |
|---|---|---|
| EP | 0 564 409 A1 | 10/1993 |
| GB | 2 398 565 A | 8/2004 |
| WO | WO 99/03854 A1 | 1/1999 |
| WO | WO 2004/106326 A1 | 12/2004 |
| WO | WO 2005/077933 A1 | 8/2005 |
| WO | WO 2005/095379 A2 | 10/2005 |

OTHER PUBLICATIONS

Choi, et al. Int. J. Miner. Process., 74S, 2004, S165-S172.*
Foreign communication from a related counterpart application—International Search Report, PCT/GB2005/003392, Dec. 15, 2005, 4 pages.
Foreign communication from a related counterpart application—International Preliminary Report on Patentability, PCT/GB2005/003392, Mar. 6, 2007, 8 pages.

* cited by examiner

*Primary Examiner* — Douglas M Willis
(74) *Attorney, Agent, or Firm* — Conley Rose, P.C.; Rodney B. Carroll

(57) ABSTRACT

The invention relates to imatinib for use in tumor therapy. This invention describes a stable, non hygroscopic alpha crystalline form of methane sulfonic acid addition salt of 4-(4-methyl piperazin-1-yl methyl)-N-[4-methyl-3-(4-pyridin-3-yl)-pyrimidin-2-yl amino) phenyl]-benzamide (imatinib mesylate) having the general structural formula

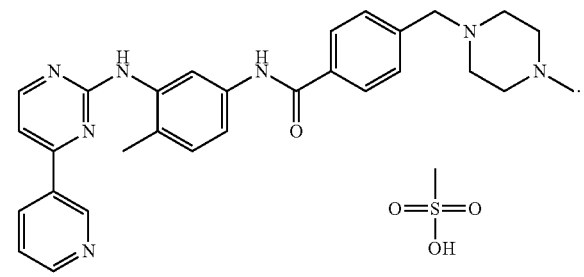

A process for the preparation of the crystalline form is also described.

8 Claims, 2 Drawing Sheets

STABLE CRYSTAL FORM OF IMATINIB MESYLATE AND PROCESS FOR THE PREPARATION THEREOF

CROSS-REFERENCE TO RELATED APPLICATIONS

Figure 1:
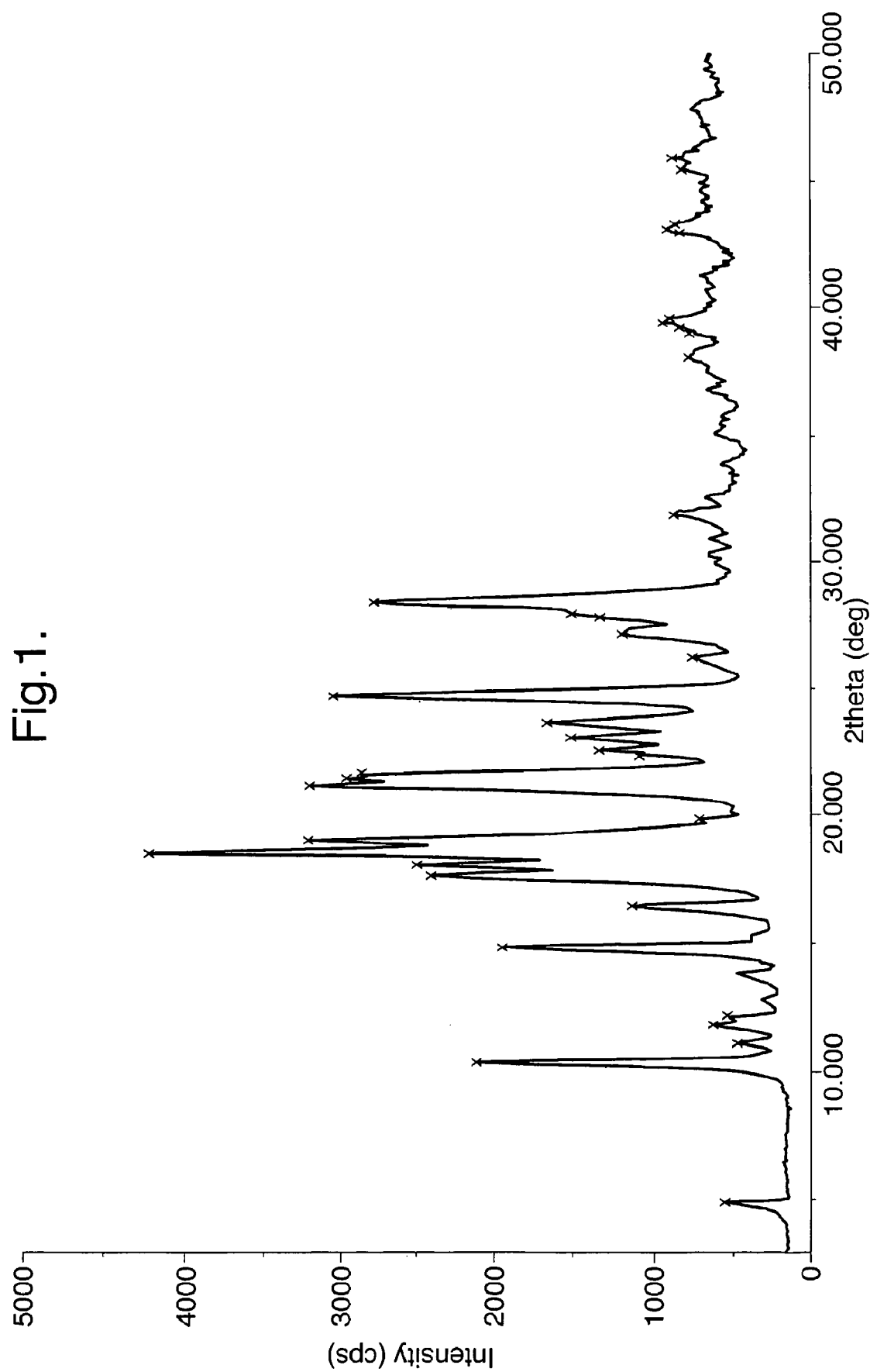

This application is a filing under 35 U.S.C. 371 of International Application No. PCT/GB2005/003392 filed Sep. 2, 2005, entitled "Stable Crystal Form of Imatinib Mesylate and Process for the Preparation Thereof," claiming priority of Indian Patent Application No. 951/MUM/2004 filed Sep. 2, 2004, which applications are incorporated by reference herein in their entirety.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION BY REFERENCE OF MATERIAL SUBMITTED ON A COMPACT DISC

Not Applicable.

BACKGROUND OF THE INVENTION

1. Field of the Invention

The present invention relates to a stable crystal form of the methane sulfonic acid addition salt of 4-(4-methyl piperazin-1-yl methyl)-N-[4-methyl-3-(4-pyridin-3-yl)-pyrimidin-2-yl amino) phenyl]-benzamide of Formula I, and to a process for the preparation thereof. The crystal form according to the invention may be used in the preparation of pharmaceutical formulations for use in tumor therapy.

2. Description of Related Art

Imatinib is the international non-proprietary name of 4-(4-methyl piperazin-1-yl methyl)-N-[4-methyl-3-(4-pyridin-3-yl)-pyrimidin-2-yl amino) phenyl]-benzamide. Imatinib is currently used for the treatment of patients with certain types of leukaemia (most commonly chronic myeloid leukaemia) and a rare type of cancer known as gastro-intestinal stromal tumour (GIST). The structural formula of imatinib is given below.

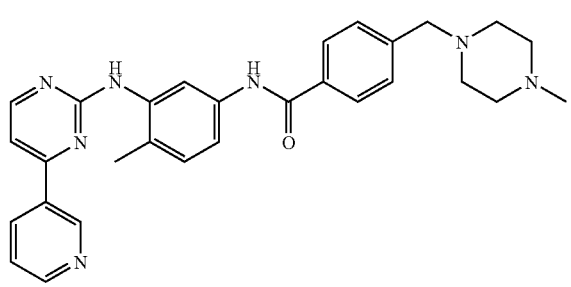

I

EP564409 and U.S. Pat. No. 5,521,184 first reported a process for preparation of 4-(4-methyl piperazin-1-yl methyl)-N-[4-methyl-3-(4-pyridin-3-yl)-pyrimidin-2-yl amino) phenyl]benzamide of Formula I and the use thereof, especially as an anti-tumor agent. However, it does not specify any crystal modifications.

Patent Application WO 99/03854 disclosed two polymorphic forms of Methane sulfonic acid addition salt of imatinib (Imatinib Mesylate) viz: an (α) Alpha crystal form and a (β) Beta crystal form and the processes for their preparation. The process for the preparation of the alpha crystalline form comprises suspending imatinib base in ethanol, adding methane sulfonic acid dropwise to the said solution, heating the solution to reflux and filtering; evaporating the filtrate to 50%, filtering off the residue; evaporating the mother liquor to dryness; suspending the residue and filtered material in ethanol; dissolving under reflux conditions by simultaneously adding water; cooling overnight, filtering and drying to obtain alpha crystalline form. The obtained alpha-crystalline form is not stable, is highly hygroscopic, is amorphous in nature and not useful for the preparation of pharmaceutical preparations.

The previously known method for producing the alpha-crystal form of methane sulfonic acid addition salt of the compound of Formula I involves the precipitation of the salt from its solution in non-alcoholic solvents. It has also been acknowledged in the prior art that the α-crystal form obtained by such a process was inconsistent and hence had an undesirable property such as hygroscopic nature and unfavourable flow characteristics. It was thus an unstable crystal form and unsuited for pharmaceutical preparations.

The known process for preparing the beta-crystal form involves use of an alcoholic solvent such as methanol or ethanol, or a mixture of acetone and water or dimethyl formamide and crystallization is induced by seeding.

BRIEF SUMMARY OF THE INVENTION

The present invention relates to a crystalline form of methane sulfonic acid addition salt of 4-(4-methylpiperazin-1-yl methyl)-N-[4-methyl-3-(4-pyridin-3-yl)-pyrimidin-2-yl amino) phenyl]-benzamide (imatinib mesylate). More specifically, the invention relates to the alpha crystalline form of imatinib mesylate.

It is important to understand that the crystalline polymorphic form of imatinib mesylate according to the invention not the same material as is described in WO 99/03854. The alpha imatinib mesylate described in WO 99/03854 is not a stable compound, whereas the alpha imatinib mesylate according to the invention is stable.

The term "stable" as used in this specification preferably means that the imatinib mesylate retains polymorphic or chemical stability for at least three months, more preferably for at least six months, and most preferably for at least twelve months. More preferably, the term "stable" as used in this specification preferably means that the imatinib mesylate retains polymorphic and chemical stability for at least three months, more preferably for at least six months, and most preferably for at least twelve months.

The invention also relates to a process for the preparation of said crystalline form of imatinib mesylate. The process according to the invention makes it possible to produce a crystalline form of methane sulfonic acid addition salt of imatinib in a form which is stable and non-hygroscopic. We have found that the stable, non-hygroscopic crystalline form of methane sulfonic acid addition salt of imatinib has needle shaped crystals. The stable, non-hygroscopic crystalline form of methane sulfonic acid addition salt of imatinib can be produced in an essentially pure crystal form.

Thus, the invention relates to a process for preparing the alpha-crystalline form of methane sulfonic acid addition salt of imatinib and also to a stable, non-hygroscopic form of the salt itself. This salt is very suitable for the preparation of pharmaceutical formulations.

BRIEF DESCRIPTION OF THE SEVERAL VIEWS OF THE DRAWING(S)

FIG. 1 shows the X-ray diffraction diagram of the alpha-crystal form of the methane sulfonic acid addition salt of compound of Formula I, according to the present invention. The X-ray diffraction diagram of the alpha-crystal form is characterized by peaks at 2-theta 4.87°, 10.40°, 18.56° and 24.82° and absence of peaks at 5.87°, 9.72° and 20.0° that are characteristic of the β-form.

Figure 2:
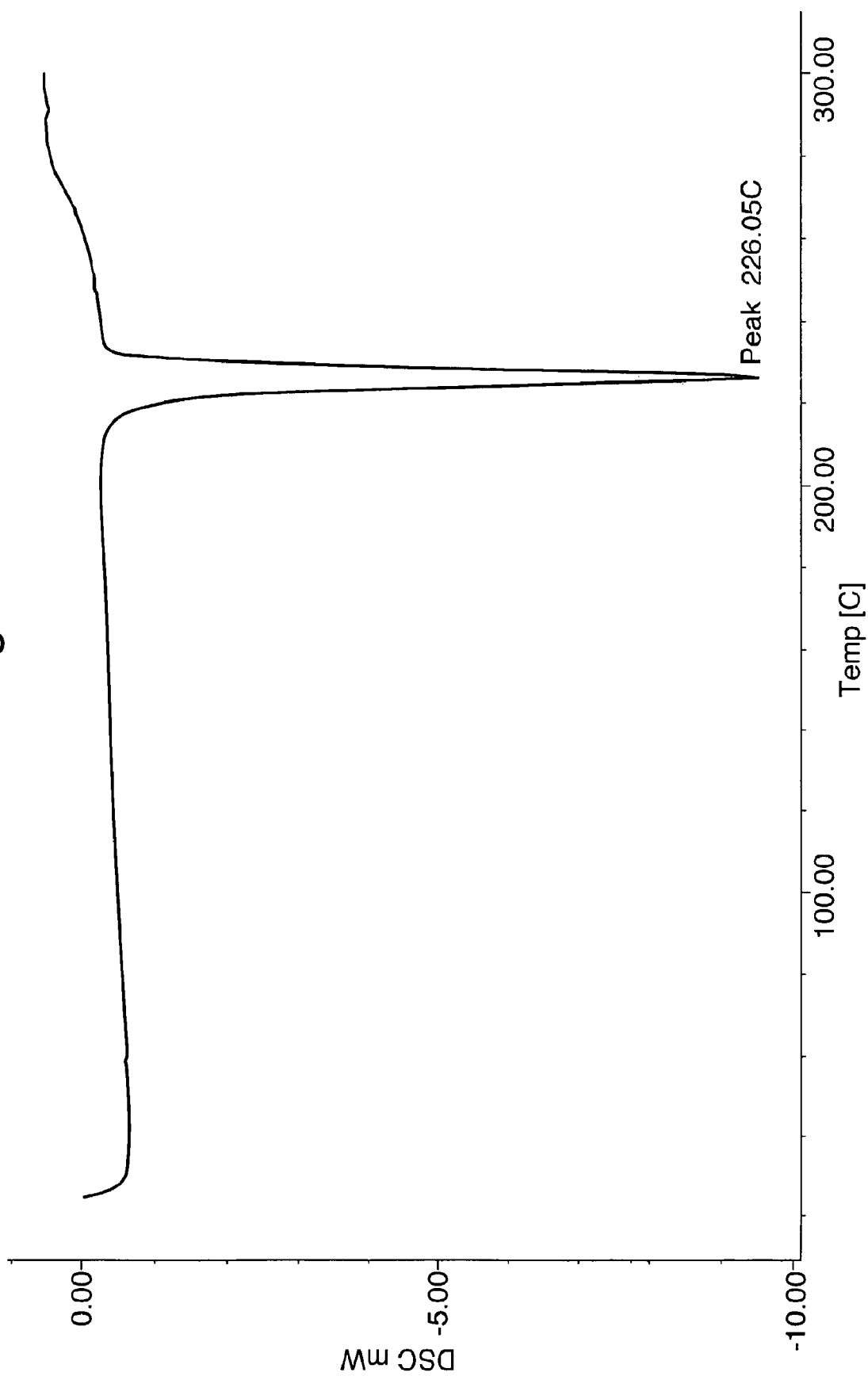

FIG. 2 shows the DSC of the alpha-crystal form of the methane sulfonic acid addition salt of compound of Formula I, according to the present invention. The alpha-crystal form of the methane sulfonic acid addition salt of a compound of Formula I according to the invention has a melting point, especially between 221-228° C. as indicated in FIG. 2.

DETAILED DESCRIPTION OF THE INVENTION

The present invention relates to a process for preparation of a stable, non-hygroscopic alpha-crystalline form of methane sulfonic acid addition salt of 4-(4-methyl piperazine-1-yl methyl)-N-[4-methyl-3-(4-pyridin-3-yl)-pyrimidin-2-yl amino) phenyl]benzamide (imatinib mesylate) of Formula I. It has also been tested and found that this form is very well suited for use in pharmaceutical formulations.

Imatinib base may be prepared according to processes described in prior art as for example in EP 564409.

According to one aspect of the present invention there is provided a process for the preparation of a pure, non-hygroscopic and stable alpha crystal form of the methane sulfonic acid addition salt of 4-(4-methyl piperazine-1-yl methyl)-N-[4-methyl-3-(4-pyridin-3-yl)-pyrimidin-2-yl amino) phenyl] benzamide of Formula II.

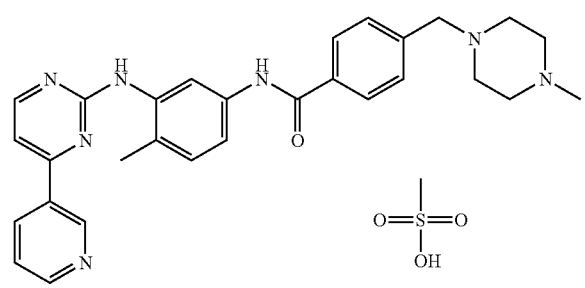

The process according to the invention is characterised by the steps of:
(a) suspending or dissolving the compound of the Formula I in a solvent;

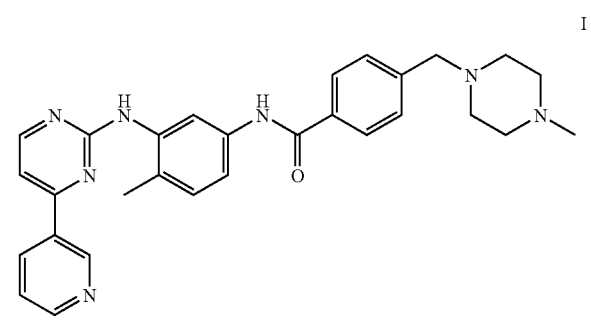

(b) adding methane sulfonic acid at a controlled rate and at predetermined temperature to above suspension or solution;
(c) heating the above mixture for a sufficient amount of time to induce the formation of alpha crystal form;
(d) cooling the mixture to ambient temperature and isolating the alpha crystal form; and, optionally,
(e) micronizing the crystals in an air jet mill to obtain the required particle size.

Preferably the cooling to ambient temperature in step (d) involves cooling to 25-30° C.

In step (b), the mixture is preferably heated to at least about 70° C., more preferably at least about 75° C., most preferably at least about 80° C.

The isolation in step (d) may be achieved by filtration, preferably followed be drying under reduced pressure. Immediately after filtration, the filtrate is preferably dissolved or suspended in a solvent, such as a $C_2$ to $C_4$ alcohol or a ketone. The solvent may be the same as the solvent used in step (a). Preferably the solvent is isopropyl alcohol.

It will be noted that the alpha crystal form of imatinib mesylate obtained by the process of the present invention involves refluxing, followed by cooling and isolation of the crystals. The contrasts with the process in WO99/03854, where the process involves refluxing, cooling, filtration, evaporation to dryness, suspension in ethanol, refluxing, adding water, cooling and filtering the alpha form. This much more complex process apparently produces the alpha form in a state which is less stable and more hygroscopic than the product produced in accordance with the process of the present invention. It will be particularly noted that an advantageous feature of the present invention is that water, per se, is not added at any stage of the process.

The present invention provides a process for producing an essentially pure alpha form of imatinib mesylate which is relatively stable (as indicated in the forced degradation studies—Table 2) which can be suited to prepare pharmaceutical formulations.

The alpha-crystal form of imatinib mesylate is characterized by needle shaped crystals. Thus, according to another aspect of the invention there is provided an crystal form (preferably alpha crystal form) of imatinib mesylate which comprises needle shaped crystals. Preferably, the crystal form (preferably alpha crystal form) of imatinib mesylate consists essentially of needle shaped crystals.

The term "essentially pure" is understood in the context of the present invention to mean especially that at least 90 wt %, preferably at least 95 wt %, and most preferably at least 99 wt % of the crystals of an acid addition salt of Formula II are present in the crystal form according to the invention, especially the α-crystal form.

In the preferred embodiment, the essentially pure methane sulfonic acid addition salt of a compound of Formula I in the alpha-crystal form shows the X-ray diffraction diagram indicated in FIG. 1. The alpha-crystal form of the methane sulfonic acid addition salt of a compound of Formula I which has a melting range, especially between 221-228° C. as indicated in FIG. 2. According to a further aspect of the invention there is provided a crystal form (preferably an alpha crystal form) or imatinib mesylate having a melting point in the range 221-228° C., or 221-225° C.

Melting points were determined by means of a DSC thermogram. DSC ["differential scanning calorimetry"] is the technique of dynamic differential calorimetry. Using this technique, the melting temperature both of the alpha-crystal form and of the beta-crystal form can be measured by heating the samples until a thermal i.e., an endothermic or exothermic, reaction is detected by means of DSC detectors. The melting point indicated in this text was determined using Schimadzu DSC 50 apparatus, about 2.0 to 3.0 mg of each sample being measured in an aluminium crucible with a perforated lid under Nitrogen atmosphere at a heating rate of 5° C./min. [starting at ambient temperature up to 300° C.].

The X-ray diffraction diagram was recorded using Rigaku Minflex (Make) with—

| | |
|---|---|
| start angle | 3.00 deg. |
| stop angle | 50.00 deg. |
| Scan speed | 2.00 deg./min. |
| Scattering | 4.2 deg. |
| Counting Unit | cps |
| XG Power | 30 KV, 15 MA |
| Divergence | Variable |
| Initial scale | 1000 cps |
| Measurement method | Continuous |
| Detector type | Scintillation counter |
| Source Cu K $\propto \lambda$ | 1.54° A |

According to another aspect of the present invention, there is provided alpha crystal form of imatinib mesylate, which can be characterised as having an X-ray diffraction pattern with characteristic peaks (2θ) as in Table 1.

TABLE 1

| Peak No. | 2θ (deg) | FWHM (deg) | d (A) | Intensity (Counts) | I/I$_0$ |
|---|---|---|---|---|---|
| 1 | 4.870 | 0.165 | 18.1296 | 573 | 14 |
| 2 | 10.400 | 0.212 | 8.4987 | 2099 | 51 |
| 3 | 11.150 | 0.318 | 7.9286 | 462 | 12 |
| 4 | 11.840 | 0.271 | 7.4681 | 640 | 16 |
| 5 | 12.130 | 0.200 | 7.2902 | 517 | 13 |
| 6 | 14.850 | 0.282 | 5.9604 | 1939 | 47 |
| 7 | 16.440 | 0.282 | 5.3874 | 1143 | 28 |
| 8 | 17.620 | 0.435 | 5.0291 | 2390 | 58 |
| 9 | 18.040 | 0.259 | 4.9130 | 2489 | 60 |
| 10 | 18.560 | 0.282 | 4.7765 | 4191 | 100 |
| 11 | 19.010 | 0.259 | 4.6644 | 3205 | 77 |
| 12 | 19.780 | 0.141 | 4.4846 | 690 | 17 |
| 13 | 21.200 | 0.294 | 4.1873 | 3197 | 77 |
| 14 | 21.480 | 0.118 | 4.1333 | 2941 | 71 |
| 15 | 21.620 | 0.176 | 4.1069 | 2832 | 68 |
| 16 | 22.400 | 0.118 | 3.9656 | 1064 | 26 |
| 17 | 22.570 | 0.188 | 3.9361 | 1320 | 32 |
| 18 | 23.090 | 0.259 | 3.8486 | 1505 | 36 |
| 19 | 23.690 | 0.271 | 3.7525 | 1657 | 40 |
| 20 | 24.820 | 0.318 | 3.5842 | 3030 | 73 |
| 21 | 26.230 | 0.200 | 3.3946 | 753 | 18 |
| 22 | 27.190 | 0.459 | 3.2769 | 1177 | 29 |
| 23 | 27.840 | 0.118 | 3.2018 | 1323 | 32 |
| 24 | 27.960 | 0.129 | 3.1884 | 1497 | 36 |
| 25 | 28.460 | 0.341 | 3.1335 | 2741 | 66 |
| 26 | 31.870 | 0.200 | 2.8056 | 852 | 21 |
| 27 | 38.000 | 0.224 | 2.3659 | 771 | 19 |
| 28 | 38.950 | 0.200 | 2.3103 | 772 | 19 |
| 29 | 39.200 | 0.106 | 2.2962 | 820 | 20 |
| 30 | 39.390 | 0.165 | 2.2855 | 918 | 22 |
| 31 | 39.550 | 0.129 | 2.2767 | 892 | 22 |
| 32 | 42.950 | 0.118 | 2.1040 | 830 | 20 |
| 33 | 43.050 | 0.200 | 2.0993 | 889 | 22 |
| 34 | 43.290 | 0.106 | 2.0882 | 856 | 21 |
| 35 | 45.540 | 0.106 | 1.9902 | 801 | 20 |
| 36 | 45.960 | 0.106 | 1.9729 | 854 | 21 |

The process of the present invention can be conveniently carried out in alcoholic or ketonic solvents. The said alcoholic solvents may be selected from $C_2$ to $C_4$ alcohols, preferably isopropanol or n-butanol. The ketonic solvent is preferably methyl-isobutyl ketone.

The preferred method of preparation comprises dissolving or suspending the compound of Formula I in the selected solvent, for example isopropanol, adding methane sulfonic acid in a controlled manner and optionally heating the contents to a temperature above ambient to the boiling point of the solvent, maintaining at the desired temperature for a fixed period of time to allow the crystallization of the methane sulfonic acid salt of Formula I to be crystallized in the desired form, followed by cooling to ambient temperature and filtering the desired crystals. The crystals may be dried at elevated temperatures under vacuum and may be further subjected to milling or micronization.

A particularly striking feature of the process according to the invention is that the product can be obtained in the desired form without resorting to seeding, which is required for producing the beta-form as disclosed in WO9903854. The process of the present invention is very suitable for industrial application, particularly as a pharmaceutical. The imatinib mesylate according to the invention is suitable for use in therapy. It is useful in methods of treating cancer, particularly leukaemia (most commonly chronic myeloid leukaemia) and GIST. It is also useful in the manufacture of a medicament for treating such diseases.

A stress study was performed on the alpha form of Imatinib Mesylate by using various conditions, such as exposure to higher temperatures, for example 60° C. for 48 hours, 105° C. for 12 hours, and UV 45° C. at 75% RH for a period of 12 hours. The study showed that the alpha imatinib mesylate produced in accordance with the present invention is quite stable as indicated Table 2 wherein there is no increase in the level of impurities before and after stability study and the product is polymorphically stable when DSC and XRPD evaluation was performed on both the samples. The product on storage was found to be stable chemically and polymorphically at ambient temperature.

Unlike many substances, which lose their polymorphic identity when subjected to stress conditions such as milling or heating, the alpha-crystals of imatinib mesylate retain the polymorphic identity thus confirming its stability under stress conditions.

Another feature of the product made by the process of the present invention is its stability to degradation conditions such as heat and humidity.

EXAMPLES

The invention will now be further described in the following examples, which are intended to illustrate the invention.

Example 1

100 gms of 4-(4-methyl piperazin-1-yl methyl)-N-[4-methyl-3-(4-pyridin-3-yl)-pyrimidin-2-yl amino) phenyl]-benzamide is added to 1500 ml of isopropyl alcohol. To this mixture, 20 gm of Methane sulfonic acid is slowly added at ambient temperature, refluxed for 2 hours, cooled to 25 to 30° C., filtered and washed with isopropyl alcohol, dried under reduced pressure at 45 to 50° C. to obtain 110 g of Imatinib mesylate alpha-form.

Example 2

17 kg of 4-(4-methyl piperazin-1-yl methyl)-N-[4-methyl-3-(4-pyridin-3-yl)-pyrimidin-2-yl amino) phenyl]-benzamide is added to 255 liters of isopropyl alcohol. To this mixture, 3.4 kg of Methane sulfonic acid is slowly added at 25 to 30° C., maintained at 75 to 80° C. for 1 hour, cooled to 25 to 30° C. filtered, washed with isopropyl alcohol and dried under reduced pressure at 45 to 50° C. obtain 19.5 kg of Imatinib mesylate alpha-form. The product is then micronized in an air-jet mill to obtain a uniform particle size of less than 25 microns.

Example 3

100 gms of 4-(4-methyl piperazin-1-yl methyl)-N-[4-methyl-3-(4-pyridin-3-yl)-pyrimidin-2-yl amino) phenyl]-benzamide is added to 1800 ml of n-butyl alcohol. To this mixture, 20 gm of Methane sulfonic acid is slowly added at ambient temperature, heated to 80° C. and maintained for 2 hours, cooled to 25 to 30° C., filtered and washed with n-butyl alcohol, dried under reduced pressure at 45 to 50° C. obtain 115 g of Imatinib mesylate alpha-form.

Example 4

Forced degradation study of imatinib mesylate (alpha form).

TABLE 2

| BATCH NO. | STRESS CONDITION | DESCRIPTION | Impurity Profile of the material in stress conditions | | | |
|---|---|---|---|---|---|---|
| | | | Single Max. impurity | Purity | DSC | XRPD |
| RD/IMT-4/31 | As such (i.e. no stress condition) | Pale yellow coloured powder | 0.18% | 99.45% | Complies | Complies |
| | 60° C. for 48 hours | Pale yellow coloured powder | 0.20% | 99.44% | Complies | Complies |
| | 105° C. for 12 hours | Pale yellow coloured powder | 0.17% | 99.49% | Complies | Complies |
| | UV −45° C. 75 RH for 12 hours | Pale yellow coloured powder | 0.19% | 99.38% | Complies | Complies |
| RD/IMT-4/34 | As such (i.e. no stress condition) | Cream coloured powder | 0.33% | 99.26% | Complies | Complies |
| | 60° C. for 48 hours | Cream coloured powder | 0.30% | 99.17% | Complies | Complies |
| | 105° C. for 12 hours | Cream coloured powder | 0.32% | 99.18% | Complies | Complies |
| | UV −45° C. 75 RH for 12 hours | Cream coloured powder | 0.34% | 99.18% | Complies | Complies |

Example 5

The stability of the imatinib mesylate according to the invention was studied over a twelve month period, to ensure that the product had chemical and polymorphic stability. This study confirmed that the imatinib mesylate retained the same polymorphic and chemical identity at six and twelve months after manufacture.

The water content of the batch of imatinib mesylate was found to vary as follows:

| | |
|---|---|
| Initial water content: | 0.39 wt % |
| Water content after 6 months: | 0.61 wt % |
| Water content after 12 months: | 0.58 wt % |

The HPLC total impurity content of the batch of imatinib mesylate was found to vary as follows:

| | |
|---|---|
| Initial total impurity content: | 0.50 wt % |
| Total impurity content after 6 months: | 0.33 wt % |
| Total impurity content after 12 months: | 0.41 wt % |

The HPLC single maximum impurity content of the batch of imatinib mesylate was found to vary as follows:

| | |
|---|---|
| Initial single maximum impurity content: | 0.23 wt % |
| Single maximum impurity content after 6 months: | 0.11 wt % |
| Single maximum total impurity content after 12 months: | 0.15 wt % |

From these measurements, it could be determined that the imatinib mesylate according to the invention is substantially polymorphically and chemically pure.

It will be appreciated that the invention described above may be modified within the scope of the claims.

The invention claimed is:

1. A process for the preparation of the alpha crystal form of the compound of Formula II:

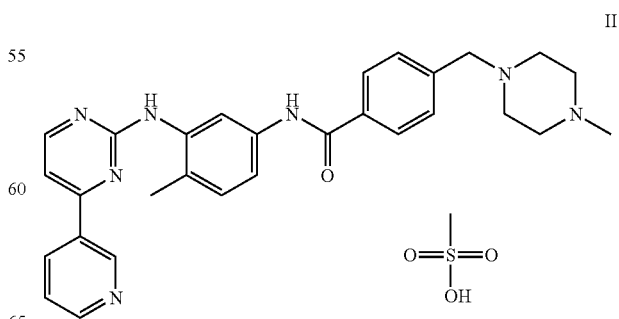

wherein the process comprises:

(a) suspending or dissolving the compound of the Formula I in a solvent;

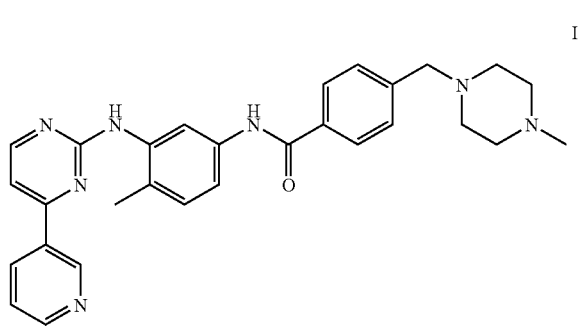

(b) adding methane sulfonic acid at a temperature of 25° C. to 30° C. to the suspension or solution formed in step (a);

(c) heating the mixture formed in step (b) to at least 70° C. for 1 to 2 hours; and (d) cooling the mixture to ambient temperature and isolating the alpha crystal form of the compound of Formula II wherein the alpha crystal form of the compound of Formula II is a stable crystal form and wherein the alpha crystal form of the compound of Formula II is characterised by an X-ray diffraction pattern having peaks at 2-theta 4.87°, 10.40°, 18.56° and 24.82° and absence of peaks at 5.87°, 9.72° and 20.0°.

2. The process according to claim 1, wherein the solvent is an alcohol or a ketone.

3. The process according to claim 2, wherein the alcohol is a $C_2$ to $C_4$ alcohol.

4. The process according to claim 1, wherein the solvent is selected from isopropanol, n-propanol, n-butanol, t-butanol or methyl isobutyl ketone.

5. The process according to claim 1 wherein the mixture formed in step (b) is heated to at least 80° C. in step (c).

6. The process according to claim 1, further comprising (e) micronizing the alpha crystal form of the compound of formula II in an air jet mill to obtain a particle size of less than 25 microns.

7. The process according to claim 1 wherein the alpha crystal form of the compound of formula II is further characterized by a differential scanning thermogram according to FIG. 2.

8. A process for the preparation of the alpha crystal form of the compound of Formula II:

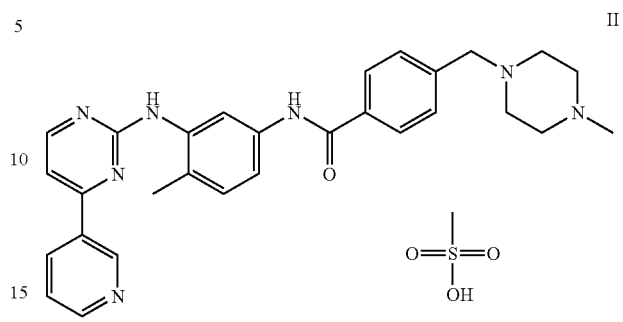

wherein the process comprises:
(a) suspending or dissolving the compound of the Formula I in a solvent;

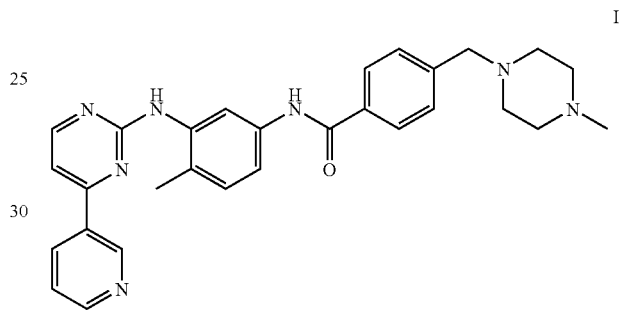

(b) adding methane sulfonic acid at a temperature of 25° C. to 30° C. to the suspension or solution formed in step (a);

(c) heating the mixture formed in step (b) to at least 70° C. for 1 to 2 hours; and (d) cooling the mixture to ambient temperature and isolating the alpha crystal form of the compound of Formula II wherein the alpha crystal form of the compound of Formula II is a stable crystal form and has an X-ray diffraction pattern having peaks at 2-theta 4.870°, 10.400°, 11.150°, 11.840°, 12.130°, 14.850°, 16.440°, 17.620°, 18.040°, 18.560°, 19.010°, 19.780°, 21.200°, 21.480°, 21.620°, 22.400°, 22.570°, 23.090°, 23.690°, 24.820°, 26.230°, 27.190°, 27.840°, 27.960°, 28.460°, 31.870°, 38.000°, 38.950°, 39.200°, 39.390°, 39.550°, 42.950°, 43.050°, 43.290°, 45.540° and 45.960°.

\* \* \* \* \*